(12) United States Patent
Lee

(10) Patent No.: US 11,561,165 B2
(45) Date of Patent: Jan. 24, 2023

(54) BIOMETRIC SYSTEM

(71) Applicant: TASCOM CO., LTD., Anyang-si (KR)

(72) Inventor: Sung-Dong Lee, Gyeonggi-do (KR)

(73) Assignee: TASCOM CO., LTD., Anyang-si (KR)

( * ) Notice: Subject to any disclaimer, the term of this patent is extended or adjusted under 35 U.S.C. 154(b) by 985 days.

(21) Appl. No.: 16/076,224

(22) PCT Filed: Feb. 11, 2016

(86) PCT No.: PCT/KR2016/001394
§ 371 (c)(1),
(2) Date: Aug. 7, 2018

(87) PCT Pub. No.: WO2017/138670
PCT Pub. Date: Aug. 17, 2017

(65) Prior Publication Data
US 2020/0173909 A1 Jun. 4, 2020

(51) Int. Cl.
*G01N 21/03* (2006.01)
*G01N 21/11* (2006.01)
(Continued)

(52) U.S. Cl.
CPC ............. *G01N 21/03* (2013.01); *G01N 21/11* (2013.01); *G01N 21/75* (2013.01);
(Continued)

(58) Field of Classification Search
CPC ........ G01N 21/03; G01N 21/11; G01N 21/75; G01N 33/6827; G01N 33/70; G01N 2201/0227; G01N 33/48; G01N 21/01
See application file for complete search history.

(56) References Cited

U.S. PATENT DOCUMENTS

| 5,077,013 A | 12/1991 | Guigan |
| 8,839,982 B1 * | 9/2014 | Anderson .......... B65D 51/2835 220/521 |

(Continued)

FOREIGN PATENT DOCUMENTS

| CN | 104203412 A | 12/2014 |
| CN | 104427929 A | 3/2015 |

(Continued)

OTHER PUBLICATIONS

International Search Report dated Oct. 12, 2016 for PCT/KR2016/001394.

(Continued)

*Primary Examiner* — Samuel P Siefke
*Assistant Examiner* — Quocan B Vo
(74) *Attorney, Agent, or Firm* — Insight Law Group, PLLC; Seung Lee

(57) ABSTRACT

The biometric system comprises: a measurement cartridge; and a meter, equipped with the measurement cartridge, for measuring an analyte present in a sample of the measurement cartridge. The measurement cartridge comprises a reagent container, a capillary module, and a reagent rod. The reagent container receives a liquid reagent and has a top sealed with a sealing film. The capillary module comprises a capillary tube which is located on an upper side of the reagent container and collects the sample by a capillary phenomenon, and the capillary tube is introduced into the reagent container by rupturing a contact portion to the sealing film by an applied pressure.

18 Claims, 16 Drawing Sheets

(51) Int. Cl.
*G01N 21/75* (2006.01)
*G01N 33/68* (2006.01)
*G01N 33/70* (2006.01)

(52) U.S. Cl.
CPC ......... *G01N 33/6827* (2013.01); *G01N 33/70* (2013.01); *G01N 2201/0227* (2013.01)

(56) References Cited

U.S. PATENT DOCUMENTS

| | | | |
|---|---|---|---|
| 9,213,043 B2 | 12/2015 | Cook et al. | |
| 9,551,661 B2 | 1/2017 | Kimura et al. | |
| 9,746,462 B2 | 8/2017 | Kasdan et al. | |
| 10,261,041 B2 | 4/2019 | Blohm et al. | |
| 2004/0161368 A1* | 8/2004 | Holtlund | G01N 21/11 422/68.1 |
| 2009/0093068 A1 | 4/2009 | Yugawa et al. | |
| 2009/0170210 A1* | 7/2009 | Fukunaga | G01N 21/03 436/149 |
| 2009/0308746 A1* | 12/2009 | Hwang | G01N 35/00069 204/407 |
| 2010/0044377 A1* | 2/2010 | Porter | B65D 51/2828 220/212 |
| 2011/0127294 A1* | 6/2011 | Pearcy | A61J 1/2089 422/501 |
| 2011/0212453 A1 | 9/2011 | Agarwal et al. | |
| 2011/0293479 A1 | 12/2011 | Hong et al. | |
| 2014/0308661 A1 | 10/2014 | Holmes et al. | |
| 2014/0315325 A1 | 10/2014 | Cobb | |
| 2014/0356941 A1 | 12/2014 | Bransky et al. | |
| 2015/0024384 A1* | 1/2015 | Peyvan | B01L 3/527 435/6.1 |
| 2015/0060303 A1 | 3/2015 | Blohm et al. | |
| 2016/0202275 A1 | 7/2016 | Bae et al. | |

FOREIGN PATENT DOCUMENTS

| | | |
|---|---|---|
| CN | 105051538 A | 11/2015 |
| JP | 2010-536015 A | 11/2010 |
| JP | 2012-122977 A | 6/2012 |
| JP | 2015-516583 A | 6/2015 |
| KR | 10-2010-0136744 A | 12/2010 |
| KR | 10-1365939 B1 | 2/2014 |
| KR | 10-1412423 B1 | 6/2014 |
| KR | 10-2014-0091607 A | 7/2014 |
| WO | 2011/100708 A2 | 8/2011 |

OTHER PUBLICATIONS

Office Action dated Jan. 29, 2020 for Korean Application No. 10-2016-0028872.

The Extended European Search Report dated Jan. 2, 2019 for European Application No. 16889977.1.

The office action dated Apr. 30, 2020 for Chinese Application No. 201680081260.3.

An office action dated Nov. 26, 2020 for Indian Application No. 201817028384.

* cited by examiner

BIOMETRIC SYSTEM

CROSS-REFERENCE TO RELATED APPLICATIONS

This application is a National Phase Entry of International Application No. PCT/KR2016/001394, filed on Feb. 11, 2016, the content of which is incorporated herein by reference in its entirety.

TECHNICAL FIELD

The present invention relates to a biometric technique.

BACKGROUND ART

Korean Patent Registration No. 10-1365939 relates to a cartridge and a biological sample component measuring apparatus for measuring a biological sample component and discloses a diagnostic tool capable of actively manipulating a fluid and transporting and mixing desired reagents and samples to measure the amount of microalbumine and creatinine in urine.

DISCLOSURE

Technical Problem

The present invention is directed to providing a biometric system capable of facilitating various biometric measurements.

Technical Solution

One aspect of the present invention provides a biometric system including a measurement cartridge and a meter equipped with the measurement cartridge and configured to measure an analyte existing in a sample of the measurement cartridge. The measurement cartridge includes: a reagent container, a capillary module, and a reagent rod. The reagent container accommodates a liquid reagent and has an upper portion sealed with a sealing film. The capillary module is located above the reagent container and includes a capillary tube for collecting a sample through capillary action, the capillary tube being introduced into the reagent container by rupturing a contact portion, which comes into contact with the capillary tube, of the sealing film with an applied pressure. The reagent rod is located above the reagent container and includes a plurality of dry reagent accommodating portions in which dry agents are accommodated, the reagent rod being introduced into the reagent container by rupturing a contact portion, which comes into contact with the reagent rod, of the sealing film by an applied pressure.

The meter may measure the analyte existing in the sample of the measurement cartridge while rotating a rotor on which the measurement cartridge is mounted in a state in which at least one of the capillary tube and the reagent rod is introduced into the reagent container.

The capillary tube of the capillary module may be introduced into the reagent container by rupturing the contact portion of the sealing film with an applied pressure such that the capillary tube does not come into direct contact with the liquid reagent. The sample in the capillary tube may be separated from the capillary tube by a centrifugal force according to rotation of the rotor, and thus may be introduced into the liquid reagent.

The dry reagent of the reagent rod may be dissolved in the liquid reagent and produce a reaction in a state in which particles of the sample coexist in the reagent container.

Some of the dry reagents accommodated in the plurality of dry reagent accommodating portions may be dissolved in the liquid reagent by coming into direct contact with the liquid reagent.

At least part of the dry reagents accommodated in the plurality of dry reagent accommodating portions may be separated by rotation of the rotor and may be dissolved in the liquid reagent.

At least parts of the plurality of dry reagent accommodating portions may be spaced apart from each other vertically, and sequentially introduced into the reagent container by an applied pressure to be sequentially dissolved in the liquid reagent.

The reagent container of the measurement cartridge may include a particle accommodating portion that accommodates the particles of the sample. The particle accommodating portion may be a recess in a portion of a bottom surface of the reagent container, or an uneven portion formed on the bottom surface of the reagent container.

The coexistence of particles of the sample in the reagent container may refer to a state in which the particles of the sample are accommodated in the particle accommodating portion.

The reagent rod may accommodate a dried protease and at least one of a ketoamine oxidase, a fructosyl-amino acid oxidase, and a fructosyl-peptide oxidase.

The reagent rod may further include a reagent rod sealing film that seals the plurality of dry agent containers.

The capillary module may further include an air outlet for discharging air in the capillary tube.

The capillary module may include: a first sample recognition electrode in contact with the air outlet; and a second sample recognition electrode spaced apart from the first sample recognition electrode and configured to be in contact with the air vent, wherein the first sample recognition electrode and the second sample recognition electrode may be electrically connected to each other due to the sample, which is introduced into and completely fills the capillary tube, and the meter may sense the electrical connection between the first sample recognition electrode and the second sample recognition electrode.

Another aspect of the present invention provides a measurement cartridge for a biometric system, the measurement cartridge including: a reagent container accommodating a liquid reagent and having an upper portion sealed with a sealing film; a capillary module located above the reagent container and including a capillary tube for collecting a sample through capillary action, the capillary tube being introduced into the reagent container by rupturing a contact portion of the sealing film by an applied pressure; and a reagent rod located above the reagent container and including a plurality of dry reagent accommodating portions in which dry agents are accommodated, the reagent rod being introduced into the reagent container by rupturing a contact portion, which comes into contact with the capillary tube, of the sealing film with an applied pressure.

Advantageous Effects

As is apparent from the disclosure, various pieces of biological data can be easily measured by making a sample, a dry reagent, and a liquid reagent react in a desired order.

MODES OF THE INVENTION

Hereinafter, the above described aspects of the present invention and other aspects will become readily apparent with reference to descriptions of the following exemplary embodiments in conjunction with the accompanying drawings. Hereinafter, detailed description of the embodiments of the present invention will be given which will enable those skilled in the art to easily understand and practice the present invention.

Figure 1:
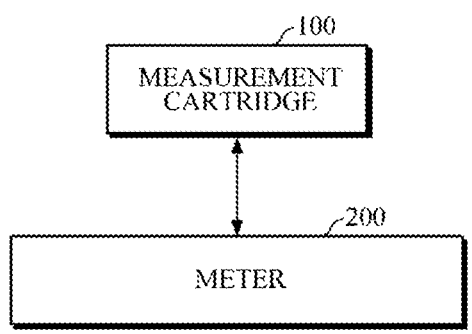
FIG. 1 is a block diagram illustrating a biometric system according to an embodiment.
Figure 2:
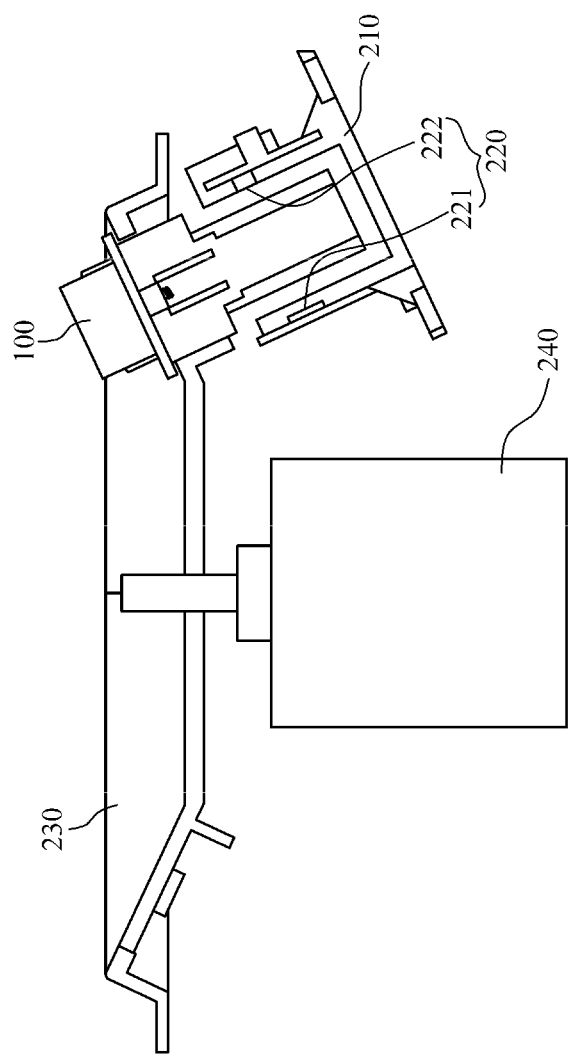
FIG. 2 is a view illustrating a schematic configuration of a biometric measurement system according to an embodiment.

FIG. 1 is a block diagram illustrating a biometric system according to an embodiment, and FIG. 2 is a reference view for describing rotation of a measurement cartridge 100 according to an embodiment. The biometric system includes a measurement cartridge 100 and a meter 200. The measurement cartridge 100 holds a sample, a dry reagent, and a liquid reagent in respective designated regions such that the sample, the dry reagent, and the liquid reagent are not mixed with each other in advance. In a state in which the measurement cartridge 100 is mounted on the meter 200, the sample and the dry reagent are introduced into the liquid reagent so that a measurement process is performed. The meter 200 performs measurement in an optical manner using an optical module 220 including a light-emitting unit 221 and a light-receiving unit 222 in a state in which the measurement cartridge 100 is mounted on a mounting portion 210. According to an aspect of the present invention, the meter 200 performs the measurement process by rotating the measurement cartridge 100. To this end, the meter 200 may include a rotor 230 and a motor 240 that rotates the rotor 230. The measurement cartridge 100 is mounted on the mounting portion 210 of the meter 200 and is rotated by the rotor 230. The meter 200 may rotate the measurement cartridge 100 in a lateral direction or move the measurement cartridge 100 to an optical measurement space of the optical module 220 by driving the motor 240 to rotate the rotor.

Figure 3:
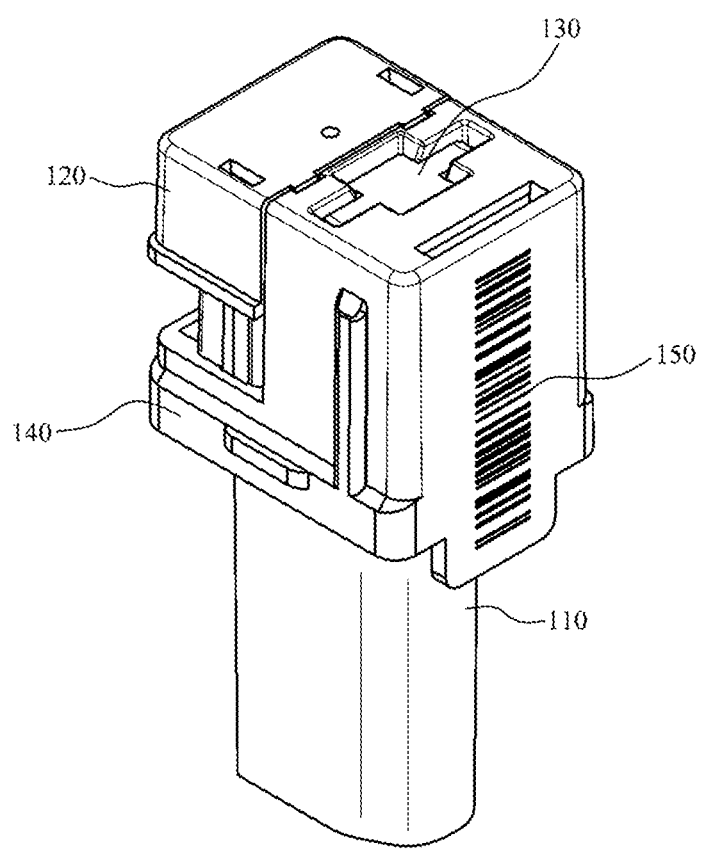
FIG. 3 is a perspective view illustrating a measurement cartridge according to an embodiment.
Figure 4:
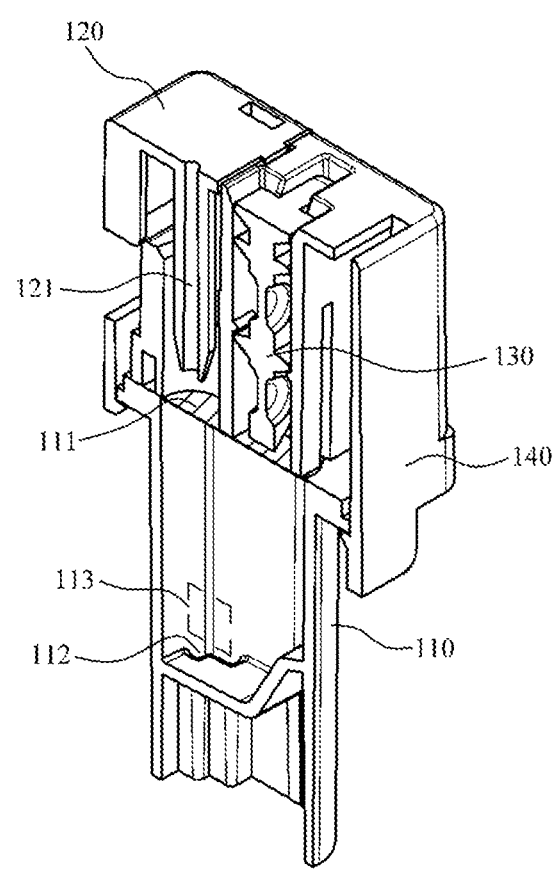
FIG. 4 is a cross-sectional view illustrating a measurement cartridge according to an embodiment.

FIG. 3 is a perspective view illustrating the measurement cartridge according to the embodiment, and FIG. 4 is a cross-sectional view illustrating the measurement cartridge according to the embodiment. The measurement cartridge 100 may include a reagent container 110, a capillary module 120, a reagent rod 130, and a housing 140. The reagent container 110 is a container formed of a transparent material used for optical measurement. The reagent container 110 accommodates a liquid reagent therein to a level such that the inner space of the reagent container 110 is not completely filled by the liquid reagent, in which the amount of the liquid reagent may be set to an amount suitable for leaving an upper portion of the inner space empty. The reagent container 110 may include a buffer, a surfactant, or a preservative, which may serve as a medium to dilute a sample, dissolve a dry reagent, and induce a reaction or combination between a sample and an analyte. In addition, particles with an antigen or an antibody immobilized therein may be introduced into the liquid reagent. The particles may be provided using latex particles, gold particles, silver particles, and magnetic particles. The liquid reagent may further include an enzyme, an enzyme substrate, a dye that reacts with an enzyme, and the like.

The reagent container 110 includes a sealing film 111. The sealing film 111 serves to seal an open upper portion of the reagent container 110 to prevent the liquid reagent from being evaporated. The sealing film 111 is preferably formed of a material which precludes permeation of a liquid and a gaseous vapor. Further, the sealing film 111 has a property of being easily punctured by the capillary module 120 and the reagent rod 130. The sealing film 111 may be combined with the reagent container 110 by a method using an adhesion, a thermal welding, an ultrasonic welding, or the like. The sealing film 111 may be provided using an aluminum foil, and in order to prevent the liquid reagent from coming into direct contact therewith, the aluminum may be coated with a polymer layer and an adhesive. In addition, a plastic film may be used as the sealing film. A barcode, a character, a number, a pattern, and the like containing information about the measurement cartridge 100 may be printed on one side of the sealing film.

In addition, the reagent container 110 may include a particle accommodating portion 112 for collecting particles. According to an embodiment, the particle accommodating portion 112 is formed on an inner bottom of the reagent container 110 and is provided in the form in which particles are precipitated and collected by the centrifugal force according to rotation of the measurement cartridge 100. For example, the particle accommodating portion 112 may be a portion of the inner bottom of the reagent container 110 that is recessed or uneven. According to another embodiment, the particle accommodating portion 112 may merely refer to an area in which particles are precipitated by a centrifugal force. Reference numeral 113 refers to a measurement area for measuring a product produced by reaction or combination between an analyte and a reagent introduced from the reagent rod 130. According to an embodiment, the reagent container 110 may only have the measurement area 113 formed of a transparent material.

The capillary module 120 includes a capillary tube 121 that collects a sample through capillary action, and the reagent rod 130 contains a dry reagent that selectively reacts or binds with an analyte in a sample. The housing 140 serves to couple the capillary module 120 and the reagent rod 130 to the reagent container 110. The capillary module 120 may be detachable from the housing 140, and the reagent rod 130 may also be detachable from the housing 140.

Meanwhile, a barcode 150 may be formed on one side of the measurement cartridge 100. As illustrated in FIG. 3, the barcode 150 may be formed on one side of the housing 140. The bar code may include information such as a lot number, a measurement item, a shelf lifetime, calibration curve information, and so on.

Figure 5:
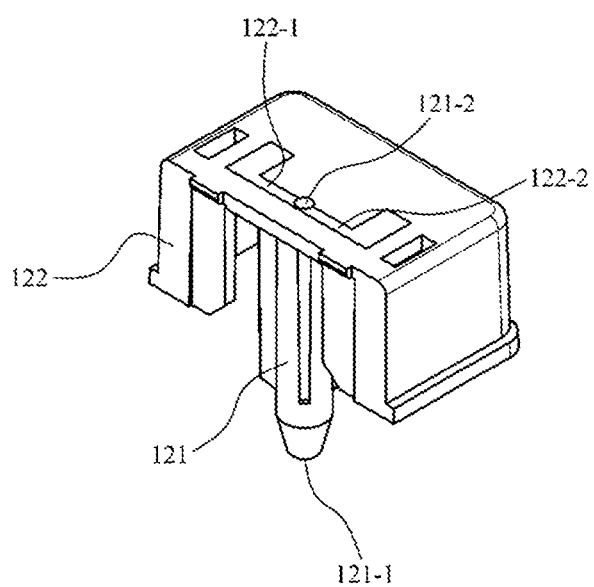
FIG. 5 is a perspective view illustrating a capillary module according to an embodiment.
Figure 6:
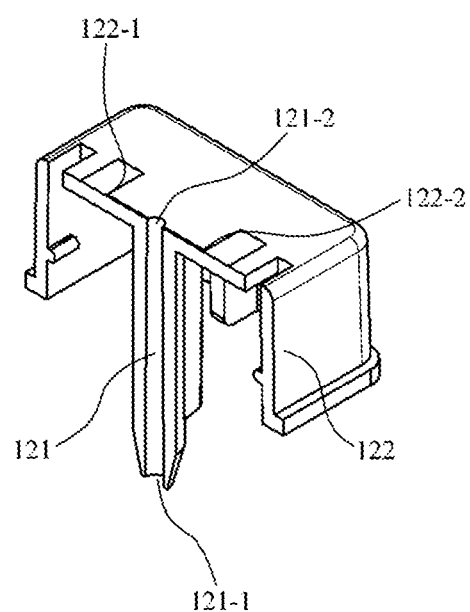
FIG. 6 is a perspective sectional view illustrating a capillary module according to an embodiment.

FIG. 5 is a perspective view illustrating the capillary module according to the embodiment, and FIG. 6 is a cross-sectional view illustrating the capillary module according to the embodiment. The capillary module 120 includes a capillary tube 121 for collecting a liquid sample using capillary action and a body 122 integrally formed with the capillary tube 121. One end of the capillary tube 121 is a sample inlet 121-1 that first comes into contact with the sample. The other end of the capillary tube 121 may be provided with an air outlet 121-2 that discharges air inside the capillary tube 121 in the process of introducing the sample into the capillary tube 121. When the sample inlet 121-1 is brought into contact with the sample, the sample is introduced into the capillary tube 121 through capillary action. In order to easily introduce the sample through capillary action, an inner wall of the capillary tube 121 may be treated with a surfactant to have a hydrophilic property.

The air outlet 121-2 of the capillary tube 121 is exposed at an upper surface of the body 122. When the body 122 is pressed, the capillary tube 121 module is moved downward and the capillary tube 121 is introduced into the reagent container 110 by penetrating the sealing film 111 of the reagent container 110. In this case, it is preferable that a rupture portion of the sealing film 111 is limited only to a portion of the sealing film 111 that comes into contact with the capillary tube 121. That is, material may be selected such that a rupture portion formed when the capillary tube 121 penetrates the sealing film 111 with a pressure applied to the body 122 has a size corresponding to that of a contact portion of the capillary tube 121. As the size of the rupture portion of the sealing film 111 is minimized corresponding to the size of the contact portion of the capillary tube 121, a sample adhering to an outer surface of the capillary tube 121 may be filtered by the sealing film 111 in contact with the outer surface. When the sample adhering to the outer surface of the capillary tube 121 is introduced into the reagent container 110, the total amount of the sample introduced into the reagent container 110 exceeds a proper amount, causing an error in the measurement result. By filtering the sample adhering to an outer surface of the capillary tube 121, only a proper amount of the sample is introduced into the reagent container 110 so that the measurement error can be prevented.

In addition, a first sample recognition electrode 122-1 and a second sample recognition electrode 122-2 may be formed on an upper surface of the body 122. The first sample recognition electrode 122-1 and the second sample recognition electrode 122-2 may be spaced apart from each other while being in contact with the air outlet 121-2. The first sample recognition electrode 122-1 and the second sample recognition electrode 122-2 are provided to prevent a risk in which an insufficient amount of sample is collected and used by a user's mistake. The sample recognition electrodes may be formed by printing a conductive ink, including silver (Ag), silver chloride (AgCl), carbon, graphite, or copper (Cu), or by sputtering conductive material, including gold (Au), indium tin oxide (ITO), or the like. According to an embodiment, a resistance or conductivity between the first sample recognition electrode 122-1 and the second sample recognition electrode 122-2 is measured while the sample inlet 121-1 of the capillary tube 121 penetrates the sealing film 111.

Figure 7:
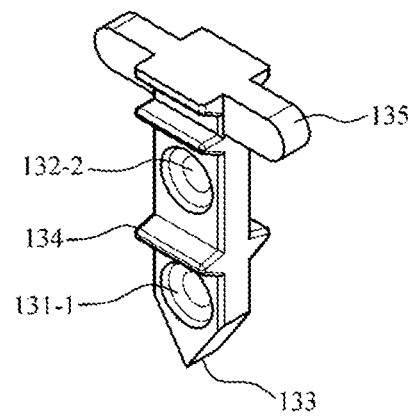
FIG. 7 is a perspective view illustrating a reagent rod according to an embodiment.
Figure 8:
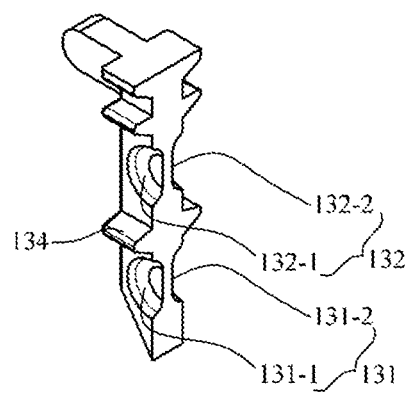
FIG. 8 is a perspective sectional view illustrating a reagent rod according to an embodiment.

FIG. 7 is a perspective view illustrating the reagent rod according to the embodiment, and FIG. 8 is a perspective sectional view illustrating the reagent rod according to the embodiment. The reagent rod may be formed of a plastic material. The reagent rod 130 includes one or more dry reagent accommodating portions. Although a total of four units of the dry agent accommodating portions are illustrated in FIG. 8, the number of the dry agent accommodating portions is not limited thereto. Each of the dry reagent accommodating portions may contain a surfactant, an enzyme, an enzyme substrate, an antibody, an antigen, an aptamer, a coloring reagent, a luminescence reagent, a fluorescent reagent, or particles with an antibody or antigen immobilized thereon in a dried state.

As shown in FIG. 8, a 1-1 dry reagent accommodating portion 131-1 and a 2-1 dry reagent accommodating portion 132-1 may be formed on one surface of the reagent rod 130 to be spaced apart from each other in a longitudinal direction of the reagent rod 130. A 1-2 dry reagent accommodating portion 131-2 and a 2-2 dry reagent accommodating portion 132-2 may be formed on the other surface of the reagent rod 130 to be spaced apart from each other in the longitudinal direction of the reagent rod 130. In a state in which the reagent rod 130 is coupled to the housing 140, the 1-1 dry reagent accommodating portion 131-1 and the 1-2 dry reagent accommodating portion 131-2 are disposed at positions lower than those of the 2-1 dry reagent accommodating portion 132-1 and the 2-2 dry reagent accommodating portion 132-2. Accordingly, the 1-1 dry reagent accommodating portion 131-1 and the 1-2 dry reagent accommodating portion 131-2 may be classified as lower dry reagent accommodating portions 131, and the 2-1 dry reagent accommodating portion 132-1 and the 2-2 dry reagent accommodating portion 132-2 may be classified as upper dry reagent accommodating portions 132.

The reagent rod 130 may further include a solution blocking portion 134 between the lower dry reagent accommodating portion 131 and the upper dry reagent accommodating portion 132. As shown in FIGS. 7 and 8, the solution blocking portion 134 serves to prevent a liquid reagent in the reagent container 110 from coming into contact with a dry reagent in the upper dry reagent accommodating portion 132 even when the liquid reagent in the reagent container 110 makes fluidic movement by rotation of the measurement cartridge 100 in a state in which only the lower dry reagent accommodating portion 131 of the reagent rod 130 is introduced into the reagent container 110. That is, even when a gap is formed in the contact portion of the sealing film 111 that comes into contact with the reagent rod 130, the solution blocking portion 134 prevents the liquid reagent from reaching the upper dry reagent accommodating portion 132 through the gap.

The reagent rod 130 may further include a rupture portion 133. The rupture portion 133 is formed in a pointed shape at one end of the reagent rod 130 at a position adjacent to the lower dry reagent accommodating portion 131. The rupture portion 133 serves to rupture the sealing film 111 of the reagent container 110 such that the reagent rod 130 penetrates the sealing film 111. Further, the reagent rod 130 may also include a guiding portion 135. The guiding portion 135 is a guiding device that allows the reagent rod 130 to be moved downward along an inner guide of the housing 140 in response to a pressure applied to a pressure application portion of the reagent rod 130 in a state in which the reagent rod 130 is mounted on the housing 140.

Different from FIG. 4, a plurality of the reagent rods 130 may be provided, and the reagent rods 130 may be mounted apart from each other on the housing 140 by a predetermined distance or more. In this case, the reagent rod 130 is provided with one or more dry reagent accommodating portions.

Figure 9:
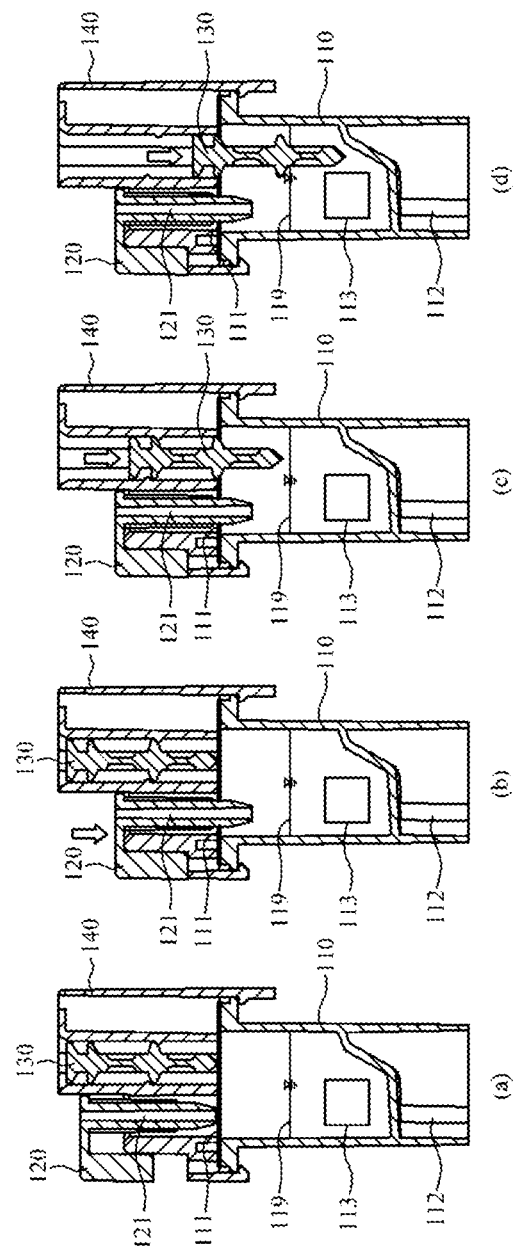
FIG. 9 is a reference view for describing operations of a measurement cartridge according to an embodiment.

FIG. 9 is a reference view for describing operations of the measurement cartridge according to the embodiment. FIG. 9A shows a state in which the housing 140 including the capillary module 120 and the reagent rod 130 is mounted above the reagent container 110. In this case, both the capillary tube 121 of the capillary module 120 and the reagent rod 130 are positioned above the sealing film 111 of the reagent container 110. When the body 122 of the capillary module 120 is pressed by a pressure, the capillary tube 121 is introduced into the reagent container 110 by penetrating the sealing film 111, as shown in FIG. 9B. When the measurement cartridge 100 is rotated while the capillary tube 121 is introduced into the reagent container 110, a sample, which the capillary tube 121 is filled with, is released to the liquid reagent by the centrifugal force.

In FIG. 9B, the capillary tube 121 may be introduced to an extent to which the sample inlet 121-1 only comes into contact with the liquid reagent accommodated in the reagent container 110, or to an extent to which the sample inlet 121-1 does not come into contact with the liquid reagent. The extent may be achieved by appropriately controlling the applied pressure. Alternatively, a step may be formed on at least one of the housing 140, the capillary module 120, and the reagent container 110 such that the extent of introduction of the capillary tube 121 is limited. Contamination or deterioration of the liquid reagent may be sensed by measuring a background signal of the liquid reagent when the capillary tube 121 is introduced into the reagent container 110 such that the sample inlet 121-1 does not come into direct contact with the liquid reagent.

Meanwhile, referring to FIG. 9C, when a pressure is applied to the pressure application portion of the reagent rod 130, the reagent rod 130 is introduced into the reagent container 110 by penetrating the sealing film 111 of the reagent container 110. In this case, the depth to which the reagent rod 130 is pressed may be adjusted such that only the lower dry reagent accommodating portion 131 is introduced into the reagent container 110, as shown in FIG. 9C. In this state, when the measurement cartridge 100 is rotated in lateral directions, the dry reagent introduced into the lower dry reagent accommodating portion 131 is dissolved in the liquid reagent by a fluctuation of the liquid reagent. The upper dry reagent accommodating portion 132 is blocked from coming into contact with the liquid reagent by the solution blocking portion 134 provided between the lower dry reagent accommodating portion 131 and the upper dry reagent accommodating portion 132. When the dry reagent introduced into the lower dry reagent accommodating portion 131 is dissolved in the liquid reagent and performs a needed function, and a pressure is further applied to the pressure application portion of the reagent rod 130, the upper dry reagent accommodating portion 132 is introduced into the reagent container 110 by penetrating the sealing film 111, as shown in FIG. 9D. In this state, when the measurement cartridge 100 is rotated in lateral directions, the dry reagent introduced into the upper dry reagent accommodating portion 132 is dissolved in the liquid reagent by a fluctuation of the liquid reagent.

For example, in the case of the measurement cartridge 100 for measuring cholesterol existing in a sample, the 1-1 dry reagent accommodating portion 131-1 includes a surfactant that dissolves lipoprotein, and the 1-2 dry reagent accommodating portion 131-2 includes a dye that reacts with peroxidase (HRP) in the presence of hydrogen peroxide ($H_2O_2$) and develops a color. The 2-1 dry reagent accommodating portion 132-1 includes a cholesterol esterase, a cholesterol oxidase, and a peroxidase (HRP) in a dried state. For example, when creatinine is measured, creatine, which is an intermediate product of creatinine existing in the sample, causes an error in measurement. For accurate measurement, there is a need for a process of removing creatine existing in the sample. To this end, the 1-1 dry reagent accommodating portion 131-1 includes a creatine amidinohydrolase enzyme, a sarcosine oxidase, and a peroxidase. The 2-1 dry reagent accommodating portion 132-1 includes a creatinine amidohydrolase enzyme, and the 2-2 dry reagent accommodating portion 132-2 includes a dye that develops a color by reacting with hydrogen peroxide and peroxidase. Referring to FIG. 9C, first, the enzymes introduced into the 1-1 dry reagent accommodating portion 131-1 are made to react with the liquid reagent, into which the sample is introduced, to remove the creatine existing in the sample, and then the creatinine amidohydrolase in the 2-1 dry reagent accommodating portion 132-1 and the dye in the 2-2 dry reagent accommodating portion 132-2 are reacted with the liquid reagent, thereby eliminating measurement errors caused by the creatine.

Meanwhile, the dry reagent accommodating portions of the reagent rod 130 may include an enzyme that selectively reacts with a measured substance existing in the sample. Examples of the enzyme may include glucose oxidase, glucose dehydrogenase, horseradish peroxidase, ascorbate oxidase, cholesterol esterase, cholesterol oxidase, creatine amidinohydrolase, diaphorase, glucose-6-phosphate dehydrogenase, glutamate dehydrogenase, glycerol kinase, glycerol dehydrogenase, hexokinase, D-3-Hydroxybutyrate dehydrogenase, lactate dehydrogenase, lipoprotein lipase, pyruvate oxidase, alkaline phosphatase, catalase, fructosylamino acid oxidase, fructosyl-peptide oxidase, urease, protease, ketoamine oxidase, hexokinase (HK), and glucose-6-phosphate dehydrogenase (G-6-PDH). The type of the enzyme is not limited thereto as long as it selectively reacts with an analyte existing in a sample.

In addition, the dry reagent accommodating portion may include a coloring dye, a fluorescent substance, and a luminescence substance for measuring a substance produced or consumed by a reaction between an analyte in a sample and an enzyme. The substance produced or consumed as a result of the reaction may be hydrogen peroxide and nicotinamide adenine dinucleotide (NADH), and the substance for measuring the produced or consumed substance may be provided using a tetrazolium derivative, for example, 2-(4-Iodophenyl)-3-(4-nitrophenyl)-5-phenyl-2H-tetrazolium chloride (INT), 3-(4,5-Dimethyl-2-thiazolyl)-2,5-diphenyl-2H-tetrazolium bromide(MTT), 3,3"-[3,3"'-Dimethoxy-(1,1'-biphenyl)-4,4'-diyl]-bis[2-(4-nitrophenyl)-5-phenyl-2H-tetrazolium chloride(Nitro-TB), 3,3"-[3,3"'-Dimethoxy-(1,1"-biphenyl)-4,4'-diyl]-bis(2,5-diphenyl-2H-tetrazolium chloride)(TB), 2-(4-Iodophenyl)-3-(4-nitrophenyl)-5-(2,4-di sulfophenyl)-2H-tetrazolium, monosodium salt(WST-1), 2-(4-Iodophenyl)-3-(2,4-dinitrophenyl)-5-(2,4-di sulfophenyl)-2H-tetrazolium, monosodium salt(WST-3), 2-Benzothiazolyl-3-(4-carboxy-2-methoxyphenyl)-5-[4-(2-sulfoethylcarbamoyl)phenyl]-2H-tetrazolium(WST-4), 2,2"-Dibenzothiazolyl-5,5'-bis[4-di(2-sulfoethyl)

carbamoylphenyl]-3,3"-(3,3"-dimethoxy 4,4"-biphenylene) ditetrazolium, disodium salt(WST-5), 4-Aminoantipyrine reacting with hydrogen peroxide, N-Ethyl-N-(2-hydroxy-3-sulfopropyl)-3-methoxyaniline, sodium salt, dehydrate(A-DOS), N-Ethyl-N-(3-sulfopropyl)-3-methoxyaniline, sodium salt, monohydrate(ADPS), N-Ethyl-N-(3-sulfopropyl)aniline, sodium salt(ALPS), 3,3'-Diaminobenzidine, tetrahydrochloride(DAB), N-Ethyl-N-(2-hydroxy-3-sulfopropyl)-3,5-dimethoxy aniline, sodium salt(DAOS), N-(2-Hydroxy-3-sulfopropyl)-3,5-dimethoxyaniline, sodium salt (HDAOS), N,N-Bis(4-sulfobutyl)-3,5-dimethyl aniline, di sodium salt(MADB), 3,3'-,5,5'-Tetramethylbenzidine (TMBZ), N,N-Bis(4-sulfobutyl)-3-methylaniline, disodium salt(TODB), N-Ethyl-N-(2-hydroxy-3-sulfopropyl)-3-methylaniline, sodium salt(TOO S), N-Ethyl-N-(3-sulfopropyl)-3-methylaniline, sodium salt(TOPS), Sodium 10-(carboxymethylaminocarbonyl)-3,7-bis(dimethylamino) phenothiazine (DA-67), N-(Carboxymethylaminocarbonyl)-4,4"-bis(dimethylamino)diphenylamine Sodium Salt(DA-64), 4-Hydroxybenzoic acid, N-Ethyl-N-(2-hydroxy-3-sulfopropyl)-3,5-dimethylaniline (MAOS), and the dry reagent accommodating portion may include 2,5-dichlorophenyldiazonium tetrafluoroborate(DPD), bromocresol green(BCG), o-Cresolphthalein Complexone, nitroblue tetrazolium(NBT), and the like that directly bind or react with an analyte in a sample to develop a color. In addition, the dry reagent accommodating portion may include various substances of enzymes, for example, ρ-Nitrophenyl phosphate, L-Alanine, α-Ketoglutarate, L-Aspartate, L-γ-Glutamyl-3-carboxy-4-nitroanilide, Glycylglycine, L-Lactate, and the like.

In addition, the dry reagent accommodating portions may include an antigen, an antibody, and an aptamer that selectively bind to an analyte in a sample and may also include a latex particle, a gold particle, a silver particle, and a magnetized magnetic particle with an antigen, an antibody, or an aptamer immobilized thereon. In addition, the dry reagent accommodating portions may include a surfactant, such as Triton X-100, bile acid, sodium cholate, Tween 20, sodium dodecyl sulfate (SDS), and the like.

According to one aspect, the dry reagent accommodating portions 131 and 132 of the reagent rod 130 may be sealed. Since reagents introduced into the dry reagent accommodating portions 131 and 132 of the reagent rod 130 in a dried state are sensitive to light or humidity, the dry reagent accommodating portions 131 and 132 may be sealed using an aluminum foil or a polymer film to protect the dry reagent from light or moisture. The sealing foil or film may be removed before the dry reagent accommodating portions 131 and 132 are inserted into the reagent container 110. Alternatively, the sealing foil or film may be removed in the course of the dry reagent accommodating portions 131 and 132 being inserted into the reagent container 110. In addition, a dehumidifying agent, such as silica gel beads or molecular sieve beads, may be introduced inside the sealing film 111 in order to keep the humidity of the dry reagent accommodating portions 131 and 132 low.

Hereinafter, a detailed measurement process using the measurement cartridge 100 will be described. When measuring glucose existing in a whole blood sample, glucose oxidase, peroxidase (HRP), and 4-aminoantipyrine in a dried state are introduced into the 1-1 dry reagent accommodating portion 131-1, and N-Ethyl-N-(2-hydroxy-3-sulfopropyl)-3,5-dimethylaniline (MAOS) in a dried state is introduced into the 2-1 dry reagent accommodating portion 132-1 or the 1-2 dry reagent accommodating portion 131-2. The reagent rod 130 provided with the dried reagents is mounted on the housing 140.

After the measurement cartridge 100 is mounted on the rotor 230 as shown in FIG. 2, the capillary module 120 is separated from the housing 140 to collect a blood sample, and then the capillary module 120 is mounted on the housing 140. In this case, the sample inlet 121-1 of the capillary tube 121 may be introduced into the reagent container 110 by penetrating the sealing film 111 of the reagent container 110 with a pressing pressure applied in the process of mounting the capillary module 120 on the housing 140, or may be introduced into the reagent container 110 using a separate pressing device provided on the meter 200. When the sample inlet 121-1 of the capillary tube 121 is introduced into the reagent container 110, the meter 200 rotates the rotor 230 such that the whole blood sample introduced into the capillary tube 121 is eluted to the liquid reagent by the centrifugal force. When the blood is eluted to the liquid reagent, the meter 200 rotates the rotor 230 in lateral directions such that the blood is completely dispersed in the liquid reagent. When the dispersion is completed, the meter 200 rotates the rotor 230 such that the measurement cartridge 100 is moved to the optical area in which the light-emitting unit 221 and the light-receiving unit 222 are provided and controls the optical module 220 to measure the amount of red blood cells. This is referred to as an erythrocyte measurement operation.

When the erythrocyte measurement is completed, the meter 200 rotates the rotor 230 to separate the red blood cells from the liquid reagent and collect the red blood cells in the particle accommodating portion 112 of the reagent container 110. When the red blood cells are separated from the liquid reagent, the meter 200 moves the measurement cartridge 100 to the optical area and measures hemolysis, turbidity, and bilirubin. This is referred to as a background signal measurement operation. When the measurement of the background signal is completed, a pressure is applied to the reagent rod 130 such that both the lower dry reagent accommodating portions 131 and the upper dry reagent accommodating portions 132 are introduced into the reagent container 110, and the rotor 230 is rotated in lateral directions to dissolve the dry reagents in the liquid reagent. With the lateral-direction rotation of the rotor 230, a fluctuation occurs in the liquid reagent, thereby allowing the dry reagents to come into contact with the liquid reagent and be dissolved in the liquid reagent, and in this process, the red blood cells collected in the particle accommodating portion 112 may be dispersed again in the liquid reagent. After an enzyme reaction is induced for a predetermined time period, the meter rotates the rotor 230 to collect the red blood cells dispersed in the liquid reagent into the particle accommodating portion 112 again, and then move the measurement cartridge 100 to the optical region to measure the amount of the dye colored by glucose. This is referred to as an analysis signal measurement operation. For reference, when the collected red blood cells are not dispersed in the liquid reagent according to the structure of the particle accommodating portion 112 even with the fluctuation of the liquid reagent, the process of rotating the rotor 230 to collect the red blood cells into the particle accommodating portion 112 again may be omitted.

The measurement of glucose existing in the whole blood sample may be affected by the amount of red blood cells existing in the whole blood sample and are also affected by hemolysis and turbidity of the whole blood sample. Accordingly, an analysis signal based on glucose should be corrected using a red blood cell measurement value or a background signal measurement value of hemolysis, turbidity, and the like.

When cholesterol is measured using the measurement cartridge 100, a surfactant that dissolves lipoprotein, such as Triton X-100, bile acid, and the like, is provided in the 1-1 dry reagent accommodating portion 131-1, and an N-Ethyl-N-(2-hydroxy-3-sulfopropyl)-3,5-dimethylaniline (MAOS) dye is provided in the 1-2 dry reagent accommodating portion 131-2. Cholesterol esterase, cholesterol oxidase, and peroxidase (HRP) are provided in the 2-1 dry reagent accommodating portion 132-1 in a dried state, and 4-Aminoantipyrine is provided in the 2-2 dry reagent accommodating portion 132-2 in a dried state. The reagent rod 130 equipped with the dry reagents is mounted on the housing 140.

After the measurement cartridge 100 is mounted on the rotor 230 as shown in FIG. 2, the capillary module 120 is separated from the housing 140 to collect a blood sample, and then the capillary module 120 is mounted on the housing 140. In this case, the sample inlet 121-1 of the capillary tube 121 may be allowed to be introduced into the reagent container 110 by penetrating the sealing film 111 of the reagent container 110 by a pressing pressure applied in the process of mounting the capillary module 120 on the housing 140 or may be introduced into the reagent container 110 using a separate pressing device provided on the meter 200. When the sample inlet 121-1 of the capillary tube 121 is introduced into the reagent container 110, the meter 200 rotates the rotor 230 such that the whole blood sample introduced into the capillary tube 121 is eluted to the liquid reagent by the centrifugal force. When the blood is eluted to the liquid reagent, the meter 200 rotates the rotor 230 in lateral directions such that the blood is completely dispersed in the liquid reagent. When the dispersion is completed, the meter 200 rotates the rotor 230 such that the measurement cartridge 100 is moved to the optical area and measures the amount of red blood cells. This is referred to as an erythrocyte measurement operation.

When the erythrocyte measurement is completed, the meter 200 rotates the rotor 230 to separate the red blood cells from the liquid reagent and collect the red blood cells in the particle accommodating portion 112 of the reagent container 110. When the red blood cells are separated from the liquid reagent, the meter 200 moves the measurement cartridge 100 to the optical area and measures hemolysis, turbidity, and bilirubin. This is referred to as a background signal measurement operation.

When the measurement of the background signal is completed, a pressure is applied to the reagent rod 130 such that both the lower dry reagent accommodating portions 131 and the upper dry reagent accommodating portions 132 are introduced into the reagent container 110, and the rotor 230 is rotated in lateral directions to dissolve the dry reagents in the liquid reagent. With the lateral-direction rotation of the rotor 230, a fluctuation occurs in the liquid reagent which causes the dry reagents to come into contact with the liquid reagent and to be dissolved in the liquid reagent, and in this process, when the red blood cells collected in the particle accommodating portion 112 are dispersed again in the liquid reagent, hemolysis may be caused by the surfactant introduced into the 1-1 dry reagent accommodating portion 131-1. When red blood cells are hemolyzed and hemoglobin is released into the liquid reagent, the red blood cells are unable to be collected into the particle accommodating portion 112 by the rotation of the rotor 230. Accordingly, the red blood cells collected in the particle receiving portion 112 should not be dispersed into the liquid reagent due to the fluctuation of the liquid reagent. Since the absorption spectrum of hemoglobin appears in the entire spectral range of UV-visible light, errors occur due to a spectrum overlap when a colorimetry method is performed. In order to prevent red blood cells collected in the particle accommodating portion 112 from being dispersed, the particle accommodating portion 112 may have a recessed structure or a concave-convex structure. After an enzyme reaction is induced for a predetermined time period, the meter 200 rotates the rotor 230 such that the measurement cartridge 100 is moved to the optical region for the amount of the dye colored by cholesterol to be measured. This is referred to as an analysis signal measurement operation. Since the amount of cholesterol existing in serum/plasma of a whole blood sample is inversely proportional to the hematocrit, the analysis signal needs to be corrected by measuring the amount of red blood cells existing in the whole blood.

When measuring glycated hemoglobin (HbA1c) using the measurement cartridge 100, the liquid agent includes a surfactant for hemolysis. Protease is provided in the 1-1 dry reagent accommodating portion 131-1 of the reagent rod 130 and, 2-(4-Iodophenyl)-3-(2,4-dinitrophenyl)-5-(2,4-disulfophenyl)-2H-tetrazolium, monosodium salt (WST-3), that is, an oxidizing agent, is provided in the 1-2 dry reagent accommodating portion 131-2. Fructosyl-amino acid oxidase or fructosyl-peptide oxidase is provided in the 2-1 dry reagent accommodating portion 132-1 together with peroxidase (HRP) in a dried state, and sodium 10-(carboxymethylaminocarbonyl)-3,7-bis(dimethylamino)phenothiazine (DA-67) is provided in the 2-2 dry reagent accommodating portion 132-2 in a dried state. The reagent rod 130 including the dry reagents is mounted on the housing 140.

After the measurement cartridge 100 is mounted on the rotor 230 as shown in FIG. 2, the capillary module 120 is separated from the housing 140 to collect a blood sample, and then the capillary module 120 is mounted on the housing 140. In this case, the sample inlet 121-1 of the capillary tube 121 may be introduced into the reagent container 110 by penetrating the sealing film 111 of the reagent container 110 by a pressing pressure applied in the process of mounting the capillary module 120 on the housing 140 or may be introduced into the reagent container 110 using a separate pressing device provided on the meter 200. When the sample inlet 121-1 of the capillary tube 121 is introduced into the reagent container 110, the meter 200 rotates the rotor 230 such that the whole blood sample introduced into the capillary tube 121 is eluted to the liquid reagent by the centrifugal force. When the blood is eluted to the liquid reagent, the meter 200 rotates the rotor 230 in lateral directions such that the blood is completely dispersed in the liquid reagent. In this process, hemolysis is caused by the surfactant existing in the liquid reagent, and thus hemoglobin is released to the liquid reagent.

When the hemolysis is completed, the meter 200 rotates the rotor 230 such that the measurement cartridge 100 is moved to the optical area and measures the amount of hemoglobin. When the measurement of hemoglobin is completed, a pressure is applied to the reagent rod 130 to introduce the 1-1 dry reagent accommodating portion 131-1 and the 1-2 dry reagent accommodating portion 131-2 into the reagent container 110. When the 1-1 dry reagent accommodating portion 131-1 and the 1-2 dry reagent accommodating portion 131-2 are introduced into the reagent container 110, the meter 200 rotates the rotor 230 in lateral directions to dissolve the protease and the WST-3. When glycated peptide or glycated amino acid, after a predetermined time of the reaction, is produced through decomposition of glycated hemoglobin (HbAlc) by the protease, the 2-1 dry reagent accommodating portion 132-1 and the 2-2 dry reagent accommodating portion 132-2 are introduced into the reagent container 110 and are brought into contact with the liquid reagent. After a predetermined time period for the reaction, hydrogen peroxide is produced by the fructosyl-amino acid oxidase or the fructosyl-peptide oxidase, and the produced hydrogen peroxide reacts with the peroxidase and the DA-67, developing a color. The meter 200 moves the measurement cartridge 100 to the optical region and measures the color development through light emission and light reception in the measurement area 113 of the reagent container 110, thereby measuring the glycated hemoglobin from the measured color development.

When an albumine creatinine ratio (ACR) is measured by measuring microalbumine and creatinine existing in urine in a single reagent container 110 using the measurement cartridge 100, the microalbumine is measured through an immuno-turbidimetry method, and the creatinine is measured through a Jaffe method. Since the Jaffe method is performed in an alkali state, it is preferable to measure the microalbumine first and then measure the creatinine. Latex particles, on which an antibody selectively binding to the microalbumine is immobilized, are introduced into the 1-1 dry reagent accommodating portion 131-1 of the reagent rod 130, sodium hydroxide (NaOH) in a dried state is introduced into the 2-1 dry reagent accommodating portion 132-1, and sodium picrate in a dried state is introduced into the 2-2 dry reagent accommodating portion 132-2. The reagent rod 130 equipped with the dry reagents is mounted on the housing 140.

After the measurement cartridge 100 is mounted on the rotor 230 as shown in FIG. 2, the capillary module 120 is separated from the housing 140 to collect a urine sample, and then the capillary module 120 is mounted on the housing 140. In this case, the sample inlet 121-1 of the capillary tube 121 may be introduced into the reagent container 110 by penetrating the sealing film 111 of the reagent container 110 by a pressing pressure applied in the process of mounting the capillary module 120 on the housing 140, or may be introduced into the reagent container 110 using a separate pressing device provided on the meter 200. When the sample inlet 121-1 of the capillary tube 121 is introduced into the reagent container 110, the meter 200 rotates the rotor 230 such that the urine sample introduced into the capillary tube 121 is eluted to the liquid reagent by the centrifugal force. When the urine sample is eluted to the liquid reagent, the meter 200 rotates the rotor 230 in lateral directions such that the sample is completely dispersed in the liquid reagent.

When the dispersion is completed, the meter 200 rotates the rotor 230 such that the measurement cartridge 100 is moved to the optical area and measures color, turbidity, and the like of the liquid sample into which the urine sample is introduced. A pressure is applied to the reagent rod 130 such that the 1-1 dry reagent accommodating portion 131-1 is introduced into the reagent container 110, and the latex particles with the antibody immobilized thereon are dispersed in the liquid reagent. The dispersed latex particles bind to the microalbumine existing in the liquid reagent and cause an immuno-agglutination, and thus the turbidity of the liquid reagent is increased. After the reaction takes place for a predetermined time period, the meter 200 moves the reagent container 110 to the optical region and measures the turbidity. When the measurement of microalbumin is completed, the 2-1 dry reagent portion 132-1 and the 2-2 dry reagent accommodating portion 132-2 of the reagent rod 130 are introduced into the reagent container 110, and the sodium hydroxide and the sodium picrate are dissolved in the liquid reagent. When the sodium hydroxide is dissolved in the liquid reagent, pH comes to indicate alkalinity, and the sodium picrate reacts with the creatinine in the urine sample, causing a color development. After the reaction for a predetermined time period, the meter 200 moves the reagent container 110 to the optical region and measures the color development caused by the creatinine.

Hereinafter, a measurement cartridge 100 according to another embodiment will be described. Since the basic structure of the measurement cartridge 100 including the reagent container 110, the capillary module 120, the reagent rod 130, and the housing 140 is identical to that of the previous embodiment, the same reference numerals are used to refer to the same elements, the description of the same elements will be omitted if possible, and the following description will be made in relation to distinguishing points.

Figure 10:
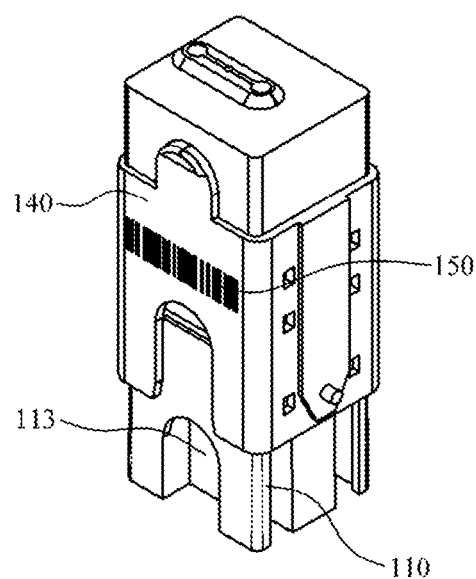
FIG. 10 is a perspective view illustrating a measurement cartridge according to another embodiment.
Figure 11:
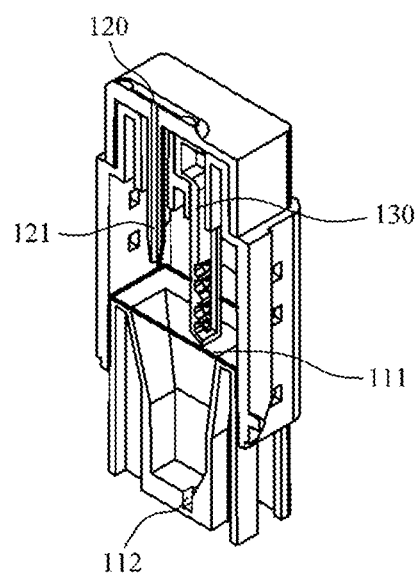
FIG. 11 is a cross-sectional view illustrating a measurement cartridge according to another embodiment.

FIG. 10 is a perspective view illustrating a measurement cartridge according to another embodiment, and FIG. 11 is a cross-sectional view illustrating the measurement cartridge according to another embodiment. Referring to FIGS. 10 and 11, a measurement cartridge 100 includes a reagent container 110, a capillary module 120, a reagent rod 130, and a housing 140. The reagent container 110 may include a particle accommodating portion 112 in which particles are accommodated, and the capillary module 120 and the reagent rod 130 may be coupled to the housing 140 to form a single body. Referring to FIGS. 10 and 11, the capillary module 120 may serve as a cover of the housing 140. The reagent rod 130 may be coupled through an upper portion or a lower portion of the housing 140. According to the embodiment, a barcode 150 may be formed on one side of the housing 140. The barcode 150 may include a Lot NO., a measurement item, a shelf lifetime, calibration curve information, and the like. Different from the measurement cartridge according to the previous embodiment, the capillary tube 121 and the reagent rod 130 are introduced into the reagent container 110 together with each other by penetrating the sealing film 111 of the reagent container 110 when a pressure is applied to the capillary module 120.

Figure 12:
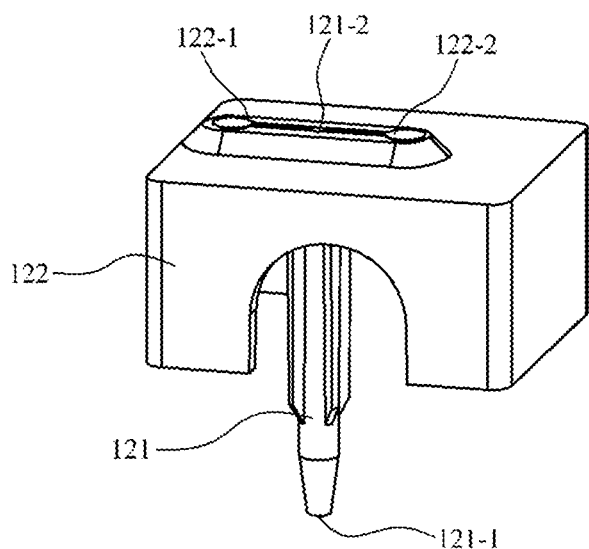
FIG. 12 is a perspective view illustrating a capillary module according to another embodiment.
Figure 13:
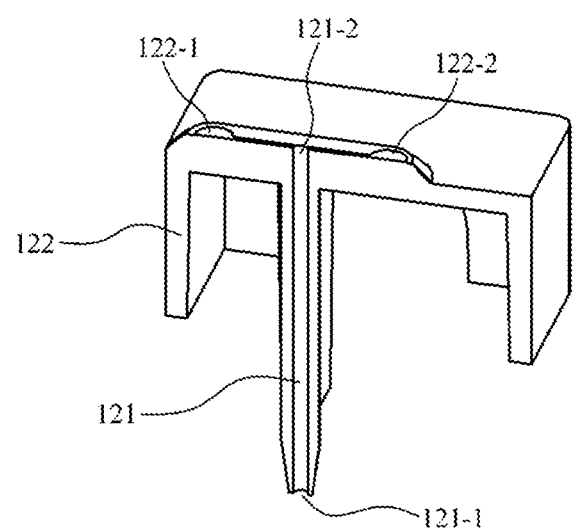
FIG. 13 is a perspective sectional view of a capillary module according to another embodiment.

FIG. 12 is a perspective view illustrating the capillary module according to another embodiment, and FIG. 13 is a perspective sectional view of the capillary module according to another embodiment. The capillary module 120 shown in FIGS. 12 and 13 has a shape slightly different from that of the capillary module 120 shown in FIGS. 5 and 6 but has the same construction. Therefore, the same description will be omitted to avoid redundancy.

Figure 14:
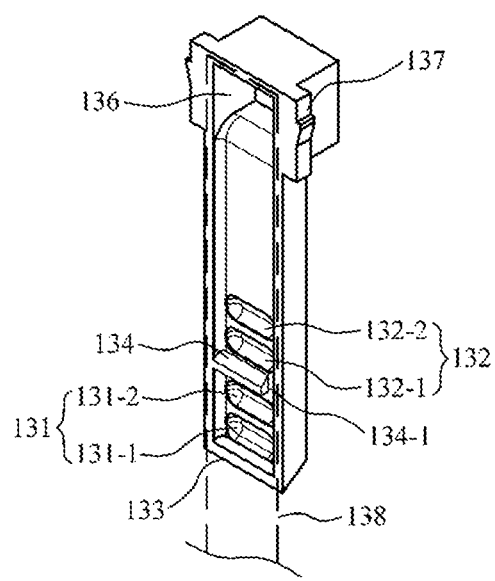
FIG. 14 is a perspective view illustrating a reagent rod according to another embodiment.

FIG. 14 is a perspective view illustrating the reagent rod according to another embodiment. The reagent rod 130 may include a lower dry reagent accommodating portion 131 and an upper dry reagent accommodating portion 132 provided on the same surface. The lower dry reagent accommodating portion 131 may include a 1-1 dry reagent accommodating portion 131-1 and a 1-2 dry reagent accommodating portion 131-2, and the upper dry reagent accommodating portion 132 may include a 2-1 dry reagent accommodating portion 132-1 and a 2-2 dry reagent accommodating portion 132-2. The reagent rod 130 is provided at a lower portion thereof with a rupture portion 133 for rupturing the sealing film 111, and at an upper portion thereof with a dehumidifying agent accommodating portion 136 for accommodating a dehumidifying agent. The reagent rod 130 may further include a solution blocking portion 134 between the lower dry reagent accommodating portion 131 and the upper dry reagent accommodating portion 132.

In addition, the reagent rod 130 may further include a reagent rod sealing film 138. The reagent rod sealing film 138 seals at least a portion of the reagent rod such that the lower dry reagent accommodating portion 131 and the upper dry reagent accommodating portion 132 are sealed together. In addition, the reagent rod sealing film 138 may seal the dehumidifying agent accommodating portion 136 as well, together with the lower dry reagent accommodating portion 131 and the upper dry reagent accommodating portion 132. An air passage 134-1 allowing air to pass therethrough may be formed on at least one portion of the solution blocking portion 134 such that the dry reagent accommodating portions 131 and 132 are kept at a low humidity while being sealed by the reagent rod sealing film 138. The dehumidifying agent accommodating portion 136 and the dry reagent accommodating portions 131 and 132 communicate with each other through the air passage 134-1.

According to one aspect, the reagent rod sealing film 138 may extend from the reagent rod 130, and an end of the extending portion may be attached to the housing 140. According to an embodiment, the end of the extending portion may be attached to an outer wall of the housing 140. This allows the reagent rod sealing film 138 to be automatically peeled off when the reagent rod 130 is introduced into the reagent container 110. Alternatively, the end of the extending portion may be attached to the reagent container 110. This also allows the reagent rod sealing film 138 to be automatically peeled off when the reagent rod 130 is introduced into the reagent container 110. As another example, the reagent rod sealing film 138 may be directly peeled off by a user. Meanwhile, an assembly guiding portion 137 is a portion for guiding the reagent rod 130 to be assembled with the housing 140.

Figure 15:
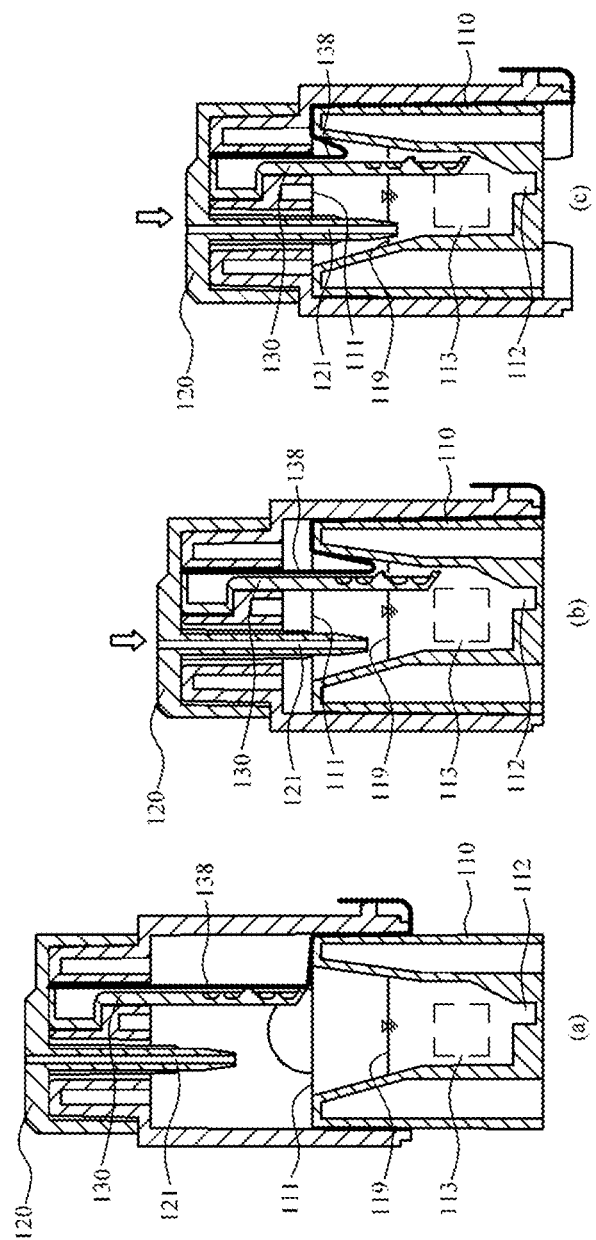
FIG. 15 is a reference view for describing operations of a measurement cartridge according to another embodiment.

FIG. 15 is a reference view for describing operations of the measurement cartridge according to another embodiment. FIG. 15A shows a state in which the housing 140 including the capillary module 120 and the reagent rod 130 is mounted above the reagent container 110. In this case, both the capillary tube 121 of the capillary module 120 and the reagent rod 130 are positioned above the sealing film 111 of the reagent container 110. When a pressure is first applied to the housing 140 in this state, the housing 140 is moved downward as shown in FIG. 9B. Accordingly, the capillary tube 121 of the capillary module 120 and the reagent rod 130 are introduced into the reagent container 110 by penetrating the sealing film 111. In FIG. 15B, only a portion of the reagent rod sealing film 138 corresponding to the lower dry reagent accommodating portion 131 may be peeled off by adjusting the depth of pressing the housing. When a pressure is further applied to the housing 140 as shown in FIG. C, the reagent rod 130 is further moved downward, causing a portion of the reagent rod sealing film 138 corresponding to the upper dry reagent accommodating portion 132 to also be peeled off. That is, the lower dry reagent accommodating portion 131 and the upper dry reagent accommodating portion 132 are sequentially exposed. Alternatively, the lower dry reagent accommodating portion 131 and the upper dry reagent accommodating portion 132 may be allowed to be exposed at once by controlling the pressing depth.

Figure 16:
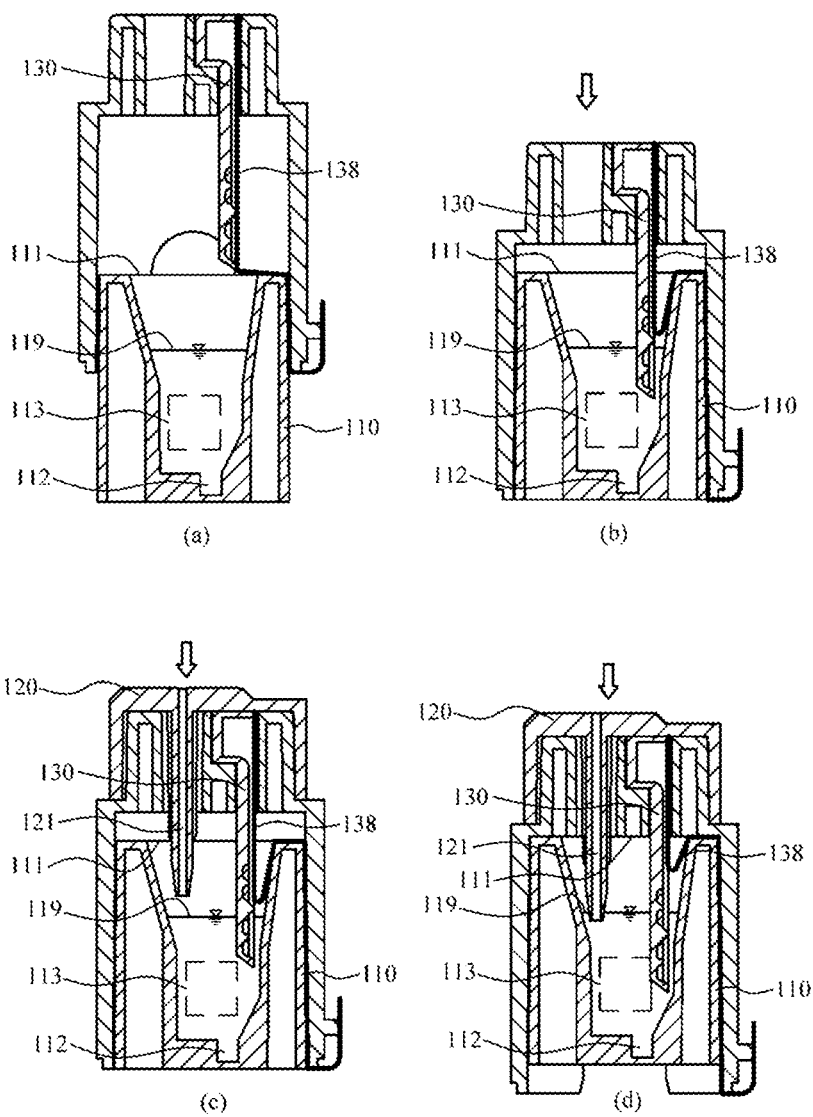
FIG. 16 is a reference view for describing operations of a measurement cartridge according to still another embodiment.

FIG. 16 is a reference view for describing operations of a measurement cartridge according to still another embodiment. FIG. 16A shows a state in which a housing 140 is mounted above a reagent container 110. The housing 140 is only equipped with a reagent rod 130 without a capillary module 120. When a pressure is first applied to the housing 140 in this state, the housing 140 is moved downward as shown in FIG. 16B. Accordingly, the reagent rod 130 is introduced into the reagent container 110 by penetrating the sealing film 111. In FIG. 16B, only a portion of a reagent rod sealing film 138 corresponding to a lower dry reagent accommodating portion 131 may be peeled off by adjusting the pressing depth. Then, as the capillary module 120 is mounted on the housing 140, the capillary module 120 is introduced into the reagent container 110 by penetrating the sealing film 111 as shown in FIG. 16C. When a pressure is further applied to the housing 140 in this state, the reagent rod 130 is moved further downward as shown in FIG. 16D, causing a portion of the reagent rod sealing film 138 corresponding to the upper dry reagent accommodating portion 132 to be peeled off.

Although the present invention has been described with reference to the exemplary embodiments, it should be understood by those of skilled in the art that changes and modifications are possible without departing from the scope and sprit of the disclosure. Therefore, the embodiments disclosed above should be considered in a descriptive sense only and not for purposes of limitation. The scope of the invention is defined not by the detailed description of the invention but by the appended claims, and encompasses all modifications and equivalents that fall within the scope of the appended claims and will be construed as being included in the present invention.

The invention claimed is:

1. A biometric system comprising:
   a measurement cartridge; and
   a meter equipped with the measurement cartridge and configured to measure an analyte existing in a sample of the measurement cartridge,
   wherein the measurement cartridge comprises:
      a reagent container configured to accommodate a liquid reagent and having an upper portion sealed with a sealing film;
      a capillary module located above the reagent container and including a capillary tube for collecting a sample through capillary action, the capillary tube being introduced into the reagent container by rupturing a contact portion, which comes into contact with the capillary tube, of the sealing film with a pressure applied thereto; and
      a reagent rod located above the reagent container and including a plurality of dry reagent accommodating portions in which dry reagents are accommodated, the reagent rod being introduced into the reagent container by rupturing a contact portion, which comes into contact with the reagent rod, of the sealing film by an applied pressure,
   wherein the reagent rod further includes solution blocking portions between the plurality of dry reagent accommodating portions, and
   wherein at least parts of the plurality of dry reagent accommodating portions are vertically arranged in the reagent rod and spaced apart from each other by the solution blocking portions, and the reagent rod is configured to move downward, in response to a pressure applied thereto, to sequentially introduce the at least parts of the plurality of dry reagent accommodating portions into the reagent container.

2. The biometric system of claim 1, wherein the meter measures the analyte existing in the sample of the measurement cartridge while rotating a rotor on which the measurement cartridge is mounted in a state in which at least one of the capillary tube and the reagent rod is introduced into the reagent container.

3. The biometric system of claim 2, wherein the capillary tube of the capillary module is introduced into the reagent container by rupturing the contact portion of the sealing film with the applied pressure to an extent to which the capillary tube does not come into direct contact with the liquid reagent.

4. The biometric system of claim 2, wherein the dry reagents of the reagent rod is dissolved in the liquid reagent and produces a reaction in a state in which particles of the sample coexist in the reagent container.

5. The biometric system of claim 2, wherein part of the dry reagents accommodated in the plurality of dry reagent accommodating portions is dissolved in the liquid reagent by coming into direct contact with the liquid reagent.

6. The biometric system of claim 2, wherein at least part of the dry reagents accommodated in the plurality of dry reagent accommodating portions is separated by rotation of the rotor and is dissolved in the liquid reagent.

7. The biometric system of claim 4, wherein the reagent container of the measurement cartridge includes a particle accommodating portion that accommodates the particles of the sample.

8. The biometric system of claim 2, wherein the reagent rod further comprises a reagent rod sealing film that seals the plurality of dry reagent accommodating portions.

9. The biometric system of claim 2, wherein the capillary module further comprises an air outlet configured to discharge air in the capillary tube.

10. The biometric system of claim 9, wherein the capillary module comprises:
   a first sample recognition electrode in contact with the air outlet; and
   a second sample recognition electrode spaced apart from the first sample recognition electrode and configured to be in contact with the air outlet,
   wherein the first sample recognition electrode and the second sample recognition electrode are electrically connected to each other by the sample introduced into the capillary tube and completely filling the capillary tube, and
   the meter senses the electrical connection between the first sample recognition electrode and the second sample recognition electrode.

11. A measurement cartridge for a biometric system, comprising:
   a reagent container configured to accommodate a liquid reagent and having an upper portion sealed with a sealing film;
   a capillary module located above the reagent container and including a capillary tube for collecting a sample through capillary action, the capillary tube being introduced into the reagent container by rupturing a contact portion, which comes into contact with the capillary tube, of the sealing film with the pressure applied thereto; and
   a reagent rod located above the reagent container and including a plurality of dry reagent accommodating portions in which dry reagents are accommodated, the reagent rod being introduced into the reagent container by rupturing a contact portion, which comes into contact with the reagent rod, of the sealing film by an applied pressure,
   wherein the reagent rod further includes solution blocking portions between the plurality of dry reagent accommodating portions, and
   wherein at least parts of the plurality of dry reagent accommodating portions are vertically arranged in the reagent rod and spaced apart from each other by the solution blocking portions, and the reagent rod is configured to move downward, in response to a pressure applied thereto, to sequentially introduce the at least parts of the plurality of dry reagent accommodating portions into the reagent container.

12. The measurement cartridge of claim 11, wherein the capillary tube of the capillary module is introduced into the reagent container by rupturing the contact portion of the sealing film by an applied pressure to an extent to which the capillary tube does not come into direct contact with the liquid reagent.

13. The measurement cartridge of claim 11, wherein the dry reagents of the reagent rod is dissolved in the liquid reagent and produces a reaction in a state in which particles of the sample coexist in the reagent container.

14. The measurement cartridge of claim 11, wherein part of the dry reagents accommodated in the plurality of dry reagent accommodating portions is dissolved in the liquid reagent by coming into direct contact with the liquid reagent.

15. The measurement cartridge of claim 11, wherein at least part of the dry reagents accommodated in the plurality of dry reagent accommodating portions is separated by rotation of the rotor and is dissolved in the liquid reagent.

16. The measurement cartridge of claim 11, wherein the reagent container of the measurement cartridge includes a particle accommodating portion that accommodates the particles of the sample.

17. The measurement cartridge of claim 11, wherein the capillary module further comprises an air outlet configured to discharge air in the capillary tube.

18. The measurement cartridge of claim 17, wherein the capillary module comprises:
   a first sample recognition electrode in contact with the air outlet; and
   a second sample recognition electrode spaced apart from the first sample recognition electrode and configured to contact with the air outlet,
   wherein the first sample recognition electrode and the second sample recognition electrode are electrically connected to each other by the sample introduced into the capillary tube and completely filling the capillary tube.

* * * * *